United States Patent
Marquant et al.

(10) Patent No.: US 11,473,118 B2
(45) Date of Patent: Oct. 18, 2022

(54) INTERFERENCE COMPENSATING TWO ELECTRODES TEST STRIP

(71) Applicant: Roche Diagnostics Operations, Inc., Indianapolis, IN (US)

(72) Inventors: Michael Marquant, Mannheim (DE); Michael Reinhardt, Mannheim (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 97 days.

(21) Appl. No.: 16/735,773

(22) Filed: Jan. 7, 2020

(65) Prior Publication Data
US 2020/0140914 A1    May 7, 2020

Related U.S. Application Data

(60) Division of application No. 15/442,202, filed on Feb. 24, 2017, now Pat. No. 10,590,458, which is a
(Continued)

(30) Foreign Application Priority Data

Aug. 25, 2014 (EP) .................................. 14182141

(51) Int. Cl.
*G01N 27/327* (2006.01)
*C12Q 1/00* (2006.01)
(Continued)

(52) U.S. Cl.
CPC ......... *C12Q 1/006* (2013.01); *G01N 27/3272* (2013.01); *G01N 27/3274* (2013.01);
(Continued)

(58) Field of Classification Search
CPC .......................................... G01N 27/327–3274
See application file for complete search history.

(56) References Cited

U.S. PATENT DOCUMENTS

| | | | |
|---|---|---|---|
| 4,919,770 | A | 4/1990 | Preidel et al. |
| 5,108,564 | A | 4/1992 | Szuminsky et al. |
| | | (Continued) | |

FOREIGN PATENT DOCUMENTS

| | | |
|---|---|---|
| CN | 1806049 | 7/2006 |
| EP | 0821234 A2 | 1/1998 |
| | (Continued) | |

OTHER PUBLICATIONS

Professional Plastics—Electrical Properties of Plastic Materials, four pages, publication date unknown, downloaded Aug. 27, 202 from https://www.professionalplastics.com/professionalplastics/ElectricalPropertiesofPlastics.pdf (Year: 2021).*

(Continued)

*Primary Examiner* — Alexander S Noguerola
(74) *Attorney, Agent, or Firm* — Woodard, Emhardt, Henry, Reeves & Wagner, LLP

(57) ABSTRACT

A method of detecting at least one analyte in a test sample is provided comprising a) contacting the test sample (i) to an active chemistry matrix changing at least one electrochemical property dependent on an enzymatic activity active in the presence of the analyte, the active chemistry matrix contacting a first electrode; and (ii) to an inactive chemistry matrix, the inactive chemistry matrix contacting a second electrode, b) closing an electrical circuit including the first electrode, the second electrode, and the active chemistry matrix and inactive chemistry matrix, followed by determining a first value of the at least one electrochemical property, c) inverting electrical polarity of the electrical circuit of b), followed by determining a second value of the at least one electrochemical property, and d) detecting the at (Continued)

least one analyte based on the first value and on the second value.

23 Claims, 4 Drawing Sheets

Related U.S. Application Data continuation of application No. PCT/EP2015/069393, filed on Aug. 25, 2015.

(51) Int. Cl.
  *G01N 33/487* (2006.01)
  *G01N 33/49* (2006.01)
(52) U.S. Cl.
  CPC . *G01N 33/48707* (2013.01); *G01N 33/48721* (2013.01); *G01N 33/49* (2013.01)

(56) References Cited

U.S. PATENT DOCUMENTS

| | | | |
|---|---|---|---|
| 5,120,420 | A | 6/1992 | Nankai et al. |
| 6,054,039 | A | 4/2000 | Shieh |
| 2005/0023152 | A1 | 2/2005 | Surridge et al. |
| 2009/0198117 | A1 | 8/2009 | Cooper et al. |
| 2009/0246808 | A1 | 10/2009 | Wilsey et al. |
| 2010/0219085 | A1 | 9/2010 | Oviatt, Jr. |
| 2013/0277234 | A1 | 10/2013 | Burke et al. |
| 2014/0001382 | A1 | 1/2014 | Loth et al. |
| 2016/0186229 | A1 | 6/2016 | Hall |

FOREIGN PATENT DOCUMENTS

| | | | |
|---|---|---|---|
| EP | 0974303 | B2 | 1/2000 |
| EP | 1457572 | | 9/2004 |
| EP | 2767826 | A1 | 8/2014 |
| JP | S63-122942 | | 5/1988 |
| JP | H06-78791 | | 3/1994 |
| JP | H08-193969 | | 7/1996 |
| JP | H09-101280 | | 4/1997 |
| JP | H10-170471 | | 6/1998 |
| JP | 2007240419 | | 9/2007 |
| JP | 2007271622 | | 10/2007 |
| JP | 2013145243 | | 7/2013 |
| JP | WO 2014/001332 | A1 | 1/2014 |
| KR | 10-2007-0022195 | | 2/2007 |
| WO | WO 2004/097035 | | 11/2004 |
| WO | WO 2005/045414 | A1 | 5/2005 |
| WO | WO 2005/045416 | A1 | 5/2005 |
| WO | WO 2007/012494 | A1 | 2/2007 |
| WO | WO 2007/071562 | A1 | 6/2007 |
| WO | WO 2008/036516 | | 3/2008 |

OTHER PUBLICATIONS

English Abstract of EP 0821234.
English Abstract of WO 2007/071562.
English Abstract of WO 200//12494.
Habermuller, Katja et al., Electron-transfer mechanisms in amperometric biosensors, Fresenius Journal of Analytical Chemistry, 2000, pp. 560-568, vol. 366.
Heller, Adam and Feldman, Ben, Electrochemical Glucose Sensors and Their Applications in Diabetes Management, Chemical Reviews, 2008, pp. 2482-2505, vol. 108.
Hoenes, Joachim et al., The Technology Behind Glucose Meters: Test Strips, Diabetes Technology & Therapeutics, 2008, pp. S-10-S-26, vol. 10, Supplement 1.
Interational Search Report dated Jun. 22, 2016, In Application No. PCT/EP2015/069393, 6 pages.
Japan Patent Application 2017-510663 Office Action dated May 16, 2019.

\* cited by examiner

INTERFERENCE COMPENSATING TWO ELECTRODES TEST STRIP

CROSS-REFERENCE TO RELATED APPLICATIONS

This application is a divisional continuation of U.S. application Ser. No. 15/442,202, filed 24 Feb. 2017, which is a continuation of International Application No. PCT/EP2015/069393, filed 25 Aug. 2015, which claims the benefit of European Patent Application No. 14182141.2, filed 25 Aug. 2014, the disclosures of which are hereby incorporated by reference in their entirety.

BACKGROUND

In the field of medical diagnostics, in many cases, one or more analytes have to be detected in test samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

Generally, devices and methods known to the skilled person make use of sensor elements (e.g., test strips) comprising one or more test chemistries, which, in the presence of the analyte to be detected, are capable of performing one or more detectable detection reactions, such as optically or electrochemically detectable detection reactions. With regard to these test chemistries and methods related thereto, reference may be made, e.g., to J. Hoenes et al. (The Technology Behind Glucose Meters: Test Strips, Diabetes Technology & Therapeutics, Volume 10, Supplement 1, 2008, S-10 to S-26, to US 2009/0246808 A1, and to Habermüller et al. ((2000), Fresenius J Anal Chem 366:560). For electrochemical detection of glucose, a review is provided, e.g., in Heller & Feldman (2008), Chem. Rev. 108: 2482. Measurement setups making use of a working electrode and a counter electrode and, optionally, a reference electrode, were, e.g., disclosed in WO 2007/071562 A1.

A common example for an amperometric glucose biosensor comprises a glucose dehydrogenase enzyme with the bound co-factor PQQ or FAD and a mediator as electron acceptor and electron shuttle in combination with noble metal or graphite electrodes. The mediator is often chosen to have low oxidation potential, so that the resulting electrode polarization is low enough to not oxidize other redox active components existing in a blood test sample, like ascorbic acid or uric acid. The disadvantage of those mediators is that, because of the described properties, they can be easily reduced by reducing agents, like ascorbic acid, contained in the blood test sample. In blood test samples from hospitalized patients, for which typically disposable test strip based professional blood glucose systems are used, the ascorbic acid concentration can be relatively high and reach levels comparable to the usual blood glucose concentrations. As a consequence, a high positively biased reading can result.

In case of enzyme systems with only temporally bound co-factors, the co-factor itself can act as an electron shuttle and, in principle, no extra redox mediator is required. An example of this is a glucose dehydrogenase enzyme with NAD as co-factor. By the enzyme reaction the NAD is reduced into NADH. Then, the NADH diffuses to the electrode and is oxidized to the radical cation. Also here, the resulting current can be measured as a measure for the glucose concentration. The disadvantage is that the NADH electrode reaction requires a high oxidation potential, which also leads to oxidation of interfering substances in the blood test sample, like ascorbic acid or uric acid. This causes high positive biased readings as well.

To overcome the above described problems, a system having two working electrodes and one reference electrode is known from WO 2005/045416 A1. The first working electrode is covered with a reagent that contains the enzyme system and the mediator as the active ingredients. The second working electrode is covered with the same reagent except the enzyme system. Both electrodes reagent layers are wetted by the same blood test sample filling a capillary measuring chamber above the electrodes. In a first phase, a voltage is applied between the reference electrode as the counter electrode and the second working electrode, which is covered with the enzyme free reagent. Then the responding current is measured. Thereafter, the voltage is applied to the reference electrode as the counter electrode and the first working electrode, which has the reagent with the enzyme system. Then the current is measured as well. If a reducing agent or electroactive component is present in the blood test sample, this would reduce the mediator or be directly oxidized at the working electrode. In both cases an interfering background current on both working electrodes is the result. The reaction with the glucose, on the other hand, only occurs on the electrode covered with the enzyme containing reagent. To get the final result, the difference of the currents measured on both working electrodes is calculated. By that calculation, the interfering effects from electrodes are extinguishing each other and, therefore, only the response from the glucose reaction remains. The limitation of this method is that both working electrodes add individual noise to the calculated results. Usually the resulting error is a geometrical sum of the individual errors. Therefore, the reachable test precision is limited. Another disadvantage with this solution is that a test strip with more than two electrodes increases the complexity and cost of the production process. In a similar approach, EP 2 767 826 A1 proposed a continuous glucose sensor comprising two working electrodes and a reference electrode, wherein the first working electrode is covered with an active enzymatic portion of a sensor membrane, whereas the second working electrode is covered with an inactive-enzymatic or non-enzymatic portion of the sensor membrane.

It is therefore an objective of the present disclosure to provide means and methods to comply with the aforementioned needs, avoiding at least in part the disadvantages of the prior art.

SUMMARY

It is against the above background that the present disclosure provides certain unobvious advantages and advancements over the prior art. In particular, the inventors have recognized a need for improvements in interference compensating two electrode test strips.

In accordance with an embodiment of the present disclosure, a method of detecting at least one analyte in a test sample is provided, said method comprising the steps of a) contacting said test sample (i) to an active chemistry matrix changing at least one electrochemical property dependent on an enzymatic activity active in the presence of said analyte, said active chemistry matrix comprising said enzymatic activity, said active chemistry matrix contacting a first electrode; and (ii) to an inactive chemistry matrix, said inactive chemistry matrix not comprising said enzymatic activity, said inactive chemistry matrix contacting a second electrode, b) closing an electrical circuit including said first electrode, said second electrode, and said active and inactive chemistry matrix, followed by determining a first value of said at least one electrochemical property, c) inverting electrical polarity of the electrical circuit of step b), followed by determining a second value of said at least one electrochemical property, and d) detecting said at least one analyte based on said first value and on said second value. Moreover, the present disclosure relates to a test device and to a test system adapted to make use of the method of the present disclosure.

In accordance with yet another embodiment of the present disclosure, a sensor element for determining at least one analyte, comprising a pair of electrodes and at least an active and an inactive chemistry matrix, said active chemistry matrix changing at least one electrochemical property dependent on an enzymatic activity active in the presence of said analyte is provided, (i) wherein said pair of electrodes consists of two electrodes electrically insulated from other electrodes, (ii) wherein said active chemistry matrix comprises said enzymatic activity and wherein said inactive chemistry matrix does not comprise said enzymatic activity, and (iii) wherein a first electrode of said pair of electrodes contacts said active chemistry matrix and wherein a second electrode of said pair of electrodes contacts said inactive chemistry matrix, wherein said sensor element does not comprise a reference electrode.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
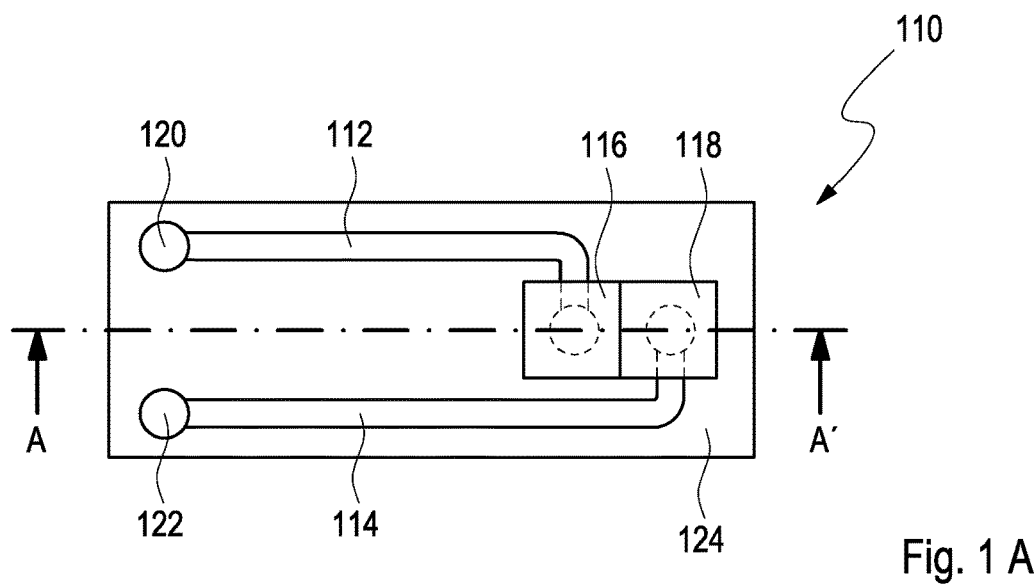
FIG. 1A shows a schematic, top view of an exemplary embodiment of a sensor element according to the present disclosure.
FIG. 1B is a cross-sectional view of the sensor element illustrated in FIG. 1A along axis A-A'.
Figure 1:
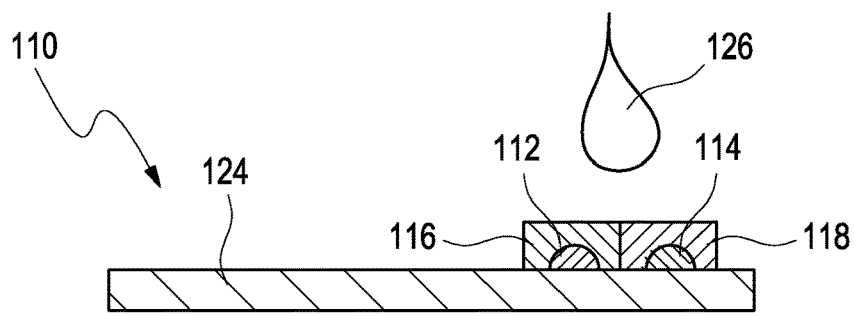

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D, or even further elements.

Further, as used in the following, the terms "preferably", "more preferably", "most preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The embodiment of the disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

The term "sensor element", as used herein relates to an element comprising at least the components as described herein. It is understood by the skilled person that the sensor element may comprise further components, e.g., without limitation, a carrier element (or "substrate") holding together other components of the sensor element; electrode contacts connecting the sensor element to a measuring device; one or more lancets for creating an incision on a body of a subject; one or more capillary elements for guiding a fluid test sample to the electrode, and the like.

The sensor element of the present disclosure comprises at least two chemistry matrices as described herein below: an active chemistry matrix comprising an enzymatic activity active in the presence of an analyte, and an inactive chemistry matrix not comprising said enzymatic activity, as specified in detail below.

In an embodiment, the sensor element further comprises a substrate. As used herein, the term "substrate" refers to a carrier element which, basically, may have an arbitrary shape, such as a strip-shape. In an embodiment, the substrate is a flexible substrate. In an embodiment, the substrate comprises a layer setup having one, two or more layers, in an embodiment, a flexible layer setup. The substrate may generally be made of any arbitrary substrate material, such as a plastic material and/or a laminate material and/or a paper material and/or a ceramic material. Other materials may be used alternatively or additionally, such as metals or thin-film setups.

The term "determining", as used herein, relates to measuring the amount of analyte in a test sample, in an embodiment, semi-quantitatively or, in a further embodiment, quantitatively. In an embodiment, determining comprises estimating the amount of electrons liberated or consumed in a chemistry matrix upon contacting a test sample with said chemistry matrix. Methods of estimating the amount of electrons liberated or consumed in a chemistry matrix are known from the prior art. In an embodiment, the amount of electrons liberated or consumed is estimated by means of an electrochemical sensor.

The term "analyte", as used herein, relates to a chemical compound present in a liquid. In an embodiment, the liquid is a test sample as specified elsewhere herein. In an embodiment, the analyte is an organic molecule, in a further embodiment, an organic molecule capable of undergoing a redox reaction in the presence of the test chemistry according to the present disclosure. In an embodiment, the analyte is a molecule of a subject's metabolism, i.e., a molecule produced by and/or consumed in at least one chemical reaction taking place in at least one tissue of said subject. Also in an embodiment, the analyte is a low molecular weight chemical compound, in a further embodiment, a chemical compound with a molecular mass of less than 5000 u (1000 Da; $1.66 \times 10^{-24}$ kg), in a further embodiment, less than 1000 u, in a further embodiment, less than 500 u. In accordance with one embodiment, the analyte is not a biological macromolecule. In a further embodiment, the analyte is selected from the list consisting of malate, ethanol, ascorbic acid, cholesterol, glycerol, urea, 3-hydroxybutyrate, lactate, pyruvate, ketones, creatinine, and the like; still in a further embodiment, the analyte is glucose. In a further embodiment, the analyte is blood glucose. In an embodiment, the analyte is blood glucose and the actual concentration to be determined is at least 10 mg/dL, at least 50 mg/dL, at least 60 mg/dL, at least 70 mg/dL, at least 80 mg/dL, at least 90 mg/dL, or at least 100 mg/dL. In an embodiment, the analyte is glucose and the concentration to be determined is in the range 0 mg/dL to 800 mg/dL, or, in a further embodiment, 10 mg/dL to 600 mg/dL, or, in a further embodiment, 50 mg/dL to 300 mg/dL.

The term "electrode" is understood by the skilled person and refers to a conductive entity of the sensor element which is adapted to get in contact with a chemistry matrix of the present disclosure. In an embodiment, the electrode is arranged such that the electrode gets in contact with at least one chemistry matrix; in a further embodiment, the electrode gets in contact with exactly one chemistry matrix. In an embodiment, the electrode is adapted to contact a liquid comprising the analyte, in an embodiment, a body fluid test sample as described elsewhere herein. The electrode may be or may comprise one or more electrode fields which fully or partially are or get in contact with the chemistry matrix and/or the liquid comprising the analyte. One or more of the electrode fields may be contacted via one or more appropriate contact leads, also referred to as conductive paths. The electrode, in an embodiment, has exactly one continuous surface area, which may be adapted to get in contact with a chemistry matrix and/or a body fluid. Each electrode may be contacted electrically by at least one contact lead. In case more than one electrode of the same type is provided, the electrodes may be contacted by one or more contact leads. Thus, two or more electrodes of the same type might be contacted electrically by one and the same contact lead. Alternatively, separate contact leads may be provided for contacting the electrodes, such as at least one separate contact lead per electrode. In an embodiment, an electrode is embodied such that an electrochemical reaction may take place at the electrode. In a further embodiment, an electrode is embodied such that an oxidation reaction and/or a reduction reaction may take place at the electrode.

In an embodiment, at least one, in a further embodiment, both of the electrodes of a pair of electrodes according to the present disclosure comprise a multi-layer setup, having at least one conductive pad and, optionally, at least one additional layer partially or, in an embodiment, fully covering the conductive pad. The at least one optional additional layer may comprise at least one electrode material as outlined in further detail below. The at least one conductive pad, in an embodiment, comprises one or more of the following metals: gold, nickel, copper or platinum, or conductive carbon allotropes like graphite or glassy carbon. However, other types of metal or conductive materials may be used in addition or alternatively. Further, a multilayer setup may be used, such as for improving an adhesion of the conductive pad to the substrate.

The conductive pad of each electrode may be connected to one or more electrical wires and/or electrical vias and/or to one or more electrical supply lines or conductor lines. Thereby, the conductive pad may be connected to at least one contact pad of the sensor element adapted for connecting the sensor element to at least one measurement device, such as a hand-held measurement device interacting with the sensor element.

As used herein, the term "pair of electrodes" relates to two electrodes adapted to be part of an electrical circuit after application of a test sample to the sensor element, said two electrodes being electrically insulated from any additional electrode potentially present in the sensor element of the present disclosure. The term "electrically insulated", as used herein, relates to separation of said pair of electrodes from any additional electrode potentially present in said sensor element such that (i) the resistance between the first electrode of the pair of electrodes and any additional electrode and (ii) the resistance between the second electrode of the pair of electrodes and any additional electrode, both are at least 25 kΩ, in an embodiment, at least 50 kΩ, in a further embodiment, at least 100 kΩ, or, in a further embodiment, at least 1MΩ after application of a test sample to the sensor element. In an embodiment, said test sample is human blood. In an embodiment, the sensor element comprises exactly one pair of electrodes as specified herein. As detailed elsewhere herein, a first electrode of a pair of electrodes (termed "analysis electrode" herein) contacts an active chemistry matrix, and a second electrode of said pair of electrodes (termed "control electrode" herein) contacts an inactive chemistry matrix.

In an embodiment, the electrodes of a pair of electrodes of the present disclosure consist of the same material or materials. Also in an embodiment, the electrodes of a pair of electrodes have the same active surface area. In a further embodiment, the electrodes of a pair of electrodes are covered with chemistry matrices of essentially the same layer thickness, "essentially the same layer thickness" meaning a difference of at most 20%, in a further embodiment, at most 10% between the active and the inactive chemistry matrix. In a further embodiment, the electrodes of a pair of electrodes are covered with chemistry matrices of the same layer thickness.

In an embodiment, at least one pair of electrodes in the sensor element of the present disclosure is arranged in a face-to-face configuration. Accordingly, the first electrode and the second electrode, in an embodiment, are arranged on opposing sides of a capillary element which is adapted to receive the sample of the body fluid and/or transport the sample of the body fluid by capillary forces. The first and the second electrode are, in an embodiment, arranged as opposing electrodes, such that a surface of the first electrode faces a surface of the second electrode. In a further embodiment, the first electrode and the second electrode are aligned in parallel. Further, the first and the second electrode may have the same dimensions and may have a non-structured shape. The first electrode may extend over a full length of the capillary. The second electrode may extend over a full length of the capillary. As used herein, the term "length of the capillary" refers to a maximum extension of the capillary in one dimension within the sensor element. In an embodiment, the capillary extends perpendicular to the elongated sensor element direction such that in this case the length of the capillary refers to a maximum extension of the capillary perpendicular to the elongated sensor element direction. In an alternative embodiment, the capillary may extend along the elongated test element direction such that in this case the length of the capillary refers to a maximum extension of the capillary along the elongated sensor element direction. The first electrode and the second electrode of a face-to-face sensor element are arranged such that during a capillary filling the first electrode and the second electrode are wetted simultaneously. An increment of a wetted surface area $dA1$ of the first electrode per increment $dV$ of a filled volume of the capillary at all times may equal an increment of a wetted surface area $dA2$ of the second electrode. As used herein, the term "capillary filling" refers to a process of receiving the sample of the body fluid. In an embodiment, the first electrode and the second electrode and the capillary in between the first electrode and the second electrode of the face-to-face sensor element form an electrochemical cell. The electrochemical cell may extend over the full length of the capillary.

As it is known to the skilled person, the term working electrode refers to an electrode being adapted for performing at least one electrochemical detection reaction for detecting the at least one analyte in a body fluid. As is further known to the skilled person, the term counter electrode refers to an electrode adapted for performing at least one electrochemical counter reaction adapted for balancing a current flow required by the detection reaction at the working electrode. The term reference electrode refers to an electrode adapted for providing a widely constant electrode potential as a reference potential, such as by providing a redox system having a constant electrode potential. According to the present disclosure, during measurements of the signal generated by the analyte and by background reactions, the analysis electrode is the working electrode and the control electrode is the counter electrode. Accordingly, during measurements of the signal generated by background reactions only, the control electrode is the working electrode and the analysis electrode is the counter electrode. Thus, in an embodiment, the sensor element does not comprise a reference electrode.

As used herein, the term "subject" relates to a vertebrate. In an embodiment, the subject is a mammal, in a further embodiment, a mouse, rat, cat, dog, hamster, guinea pig, sheep, goat, pig, cattle, or horse. Still in a further embodiment, the subject is a primate. In a further embodiment, the subject is a human. In an embodiment, the subject is afflicted or suspected to be afflicted with a disease or condition associated with a measurable deviation from normal of at least one analyte.

The term "test sample" is understood by the skilled person and relates to any suitably sized sub-portion of a tissue homogenate, tissue fluid (interstitial fluid) or body fluid of a subject.

As used herein, the term "body fluid" relates to all bodily fluids of a subject known to comprise or suspected to comprise the analyte of the present disclosure, including blood, plasma, serum, lacrimal fluid, urine, lymph, cerebrospinal fluid, bile, stool, sweat, interstitial fluid, and saliva. In an embodiment, the body fluid is blood, plasma, or serum. Body fluid test samples can be obtained by well-known techniques including, e.g., venous or arterial puncture, epidermal puncture, and the like.

The term "chemistry matrix", as used herein, refers to a matrix of compounds comprising at least one component changing at least one electrochemical property dependent on an enzymatic activity active in the presence of an analyte. Various possibilities of designing a chemistry matrix are known in the art. In this regard, reference may be made to the above-mentioned prior art documents. Specifically, reference may be made to J. Hoenes et al.: The Technology Behind Glucose Meters: Test Strips, Diabetes Technology & Therapeutics, Volume 10, Supplement 1, 2008, S-10 to S-26. However, other types of chemistry matrices are possible.

In an embodiment, the chemistry matrix of the present disclosure is adapted to change at least one electrochemical property in the presence of an analyte. As used herein, the term "electrochemical property" relates to any property of the test chemistry which changes in the presence of the analyte and which can be transferred into an electric signal of any kind. In an embodiment, the change of the electrochemical property and/or the signal generatable therefrom is proportional to the concentration of the analyte in the test sample. In an embodiment, the electrochemical property is a redox state of at least one of the components of chemistry matrix, in an embodiment, of an indicator reagent as described herein. Accordingly, in an embodiment, the detection reaction is a redox reaction. In a further embodiment, the detection reaction produces redox equivalents and/or electrons as intermediates and/or products. In a further embodiment, the electrochemical property is the concentration of a reduced or an oxidized indicator reagent as described herein, i.e., in an embodiment, the measurable property is the redox state of said indicator reagent comprised in the test chemistry. Methods of converting the electrochemical property as defined above into a physical signal which can be read as a measurement value are well known in the art and are described e.g., in EP 0 821 234, EP 0 974 303, and US 2005/0023152. In an embodiment, electrochemical properties include amperometric or coulometric responses indicative of the concentration of the analyte. See, for example, U.S. Pat. Nos. 5,108,564, 4,919,770 and 6,054,039.

The term "redox equivalents" as used herein relates to the concept commonly used in redox chemistry well known to the skilled person. In an embodiment, the term relates to electrons which are transferred from a substrate of the oxidoreductase to the redox cofactor, and/or from said redox cofactor to a redox mediator, and/or from said redox mediator to an indicator compound and/or to an electrode.

In an embodiment, the chemistry matrix is an electrochemical chemistry matrix contacting at least one electrode. Suitable electrodes, electrode setups, suitable further compounds of electrochemical test chemistry matrices and modes of operation of the same are known to the skilled person and are described, e.g., in WO 2007/071562 A1, US 2009/0198117 A1, WO 2007/071562 A1, WO 2014/001382 A1, and references cited therein. It is envisaged by the present disclosure that the electrochemical test chemistry matrix includes one or more agents for reacting with the analyte to produce an electrochemical signal that represents the presence of the analyte in the test sample fluid. It is understood by the skilled person that the chemistry matrix according to the present disclosure may have more than one layer, or, in an embodiment, one layer. Appropriate layer setups are well-known in the art.

In an embodiment, the chemistry matrix additionally comprises a redox cofactor and/or an indicator reagent capable of eliciting a change in at least one electrochemical property in the presence of redox equivalents.

The term "redox cofactor", as used herein, refers to a molecule which can serve as an acceptor for enzymatically transferred redox equivalents and, in particular, hydride (if). In an embodiment, the redox cofactor is pyrroloquinoline quinone (PQQ CAS NO: 72909-34-3), nicotina-mide adenine dinucleotide (NAD, CAS NO: 53-84-9), or flavin adenine dinucleotide (FAD, CAS NO: 146-14-5). It will be understood that the redox cofactor to be included in the test chemistry matrix of the present disclosure depends on the properties of the dehydrogenase to be envisaged. For example, PQQ is combined in a composition according to the present disclosure with a PQQ dependent dehydrogenase, NAD is combined in a composition according to the present disclosure with a NAD dependent dehydrogenase, and FAD is combined in a composition according to the present disclosure with a FAD dependent dehydrogenase. A redox cofactor according to the present disclosure may also, in an embodiment, be a derivative of PQQ, NAD or FAD. Typical derivatives of NAD are those disclosed in WO 2007/012494 which is herewith incorporated by reference with respect to the disclosed NAD/NADH and/or NADP/NADPH derivatives. In a further embodiment, the redox cofactor in accordance with the present disclosure is carbaNAD as disclosed in WO 2007/012494.

As used herein, the term "indicator reagent capable of eliciting a change in at least one electrochemical property in the presence of redox equivalents" refers to a molecule which, in the presence of redox equivalents, is capable of undergoing a change in at least one measurable property, in an embodiment, a change which can be measured as electrochemical property of the chemistry matrix.

An indicator reagent as referred to above is, in an embodiment, capable of transferring directly or indirectly, i.e., via a further mediator, redox equivalents from the redox cofactor to an electrode. In the latter case, the redox equivalents are transferred from the indicator reagent to an intermediate mediator which subsequently transfers the redox equivalents to an electrode. It will be understood that more than one mediator can be used. For example, the agent may transfer the redox equivalents to a first mediator which subsequently transfers the redox equivalents to a second mediator and said second mediator then transfers the redox equivalents to an electrode. It will be understood that in such a mediator cascade more than two mediators could be used. In a further embodiment, an indicator reagent is capable of directly transferring redox equivalents from the redox cofactor to an electrode.

Mediators that can be applied in the context of the present disclosure are well known in the art and include, e.g., potassium ferricyanide, quinone derivatives, Nile blue (CAS NO: 3625-57-8), Meldola's blue (CAS NO: 7057-57-0), osmium complexes as disclosed in EP 1 457 572 B1, transition metal complexes such as ruthenium hexamine chloride, or nitroso-aniline-derivatives.

In an embodiment of the chemistry matrix of the present disclosure, said chemistry matrix further comprises at least one stabilizer, detergent, swelling agent, film-forming agent, oxidizing agent and/or solid particle. Suitable stabilizers, detergents, swelling agents, film forming agents, oxidizing agents, and/or solid particles to be used in the composition of the disclosure are known to the skilled artisan. In an embodiment, the said at least one detergent is selected from the group consisting of: Sodium-N-methyl-N-oleoyltaurat, N-octanoyl-N-methyl-glucamid, Mega 8 (N-methyl-N-octanoylglucamide), dioctylsodium sulfosuccinate (DONS), Rhodapex® (in an embodiment, CO-433 or CO-436). In an embodiment, said at least one swelling agent is selected from the group consisting of: methyl vinyl ether maleic acid anhydride copolymer, xanthan gum and methyl vinyl ether maleic acid copolymer. In an embodiment, said at least one film-forming agent is selected from the group consisting of: polyvinylpropionate dispersions, Polyvinyl esters, polyvinyl acetates, polyacrylic esters, polymethacrylic acid, polyvinyl amides, polyamides, polystyrene and mixed polymerisates are also suitable such as of butadiene, styrene or maleic acid ester. In an embodiment, said at least one solid particle is selected from the group consisting of: silica particles, in particular, silicon dioxide, sodium silicates or aluminum silicates, kieselguhr, metal oxides, in particular, titan oxide and/or aluminum oxide, synthetic oxide materials, in particular, nanoparticles of oxide materials such as nanoparticles of silicon dioxide, aluminum oxide, or titan oxide, Kaolin, powder glass, amorphous silica, calcium sulfate, and barium sulfate.

A chemistry matrix according to the present disclosure can be provided, in an embodiment, by dissolving the components of the chemistry matrix first in a solvent or mixture of solvents. In a further embodiment, said solvent or mixture of solvents is subsequently removed by a suitable treatment such that the remaining composition is essentially free of the said solvent or solvent mixture. Suitable treatments to be, in an embodiment, envisaged by the present disclosure include heat treatment, evaporation techniques, freeze drying and the like. In an embodiment, the envisaged treatment is heat treatment and, in particular, heat treatment under the following conditions: heat treatment at about 60° C. or more for approximately 20 to 45 minutes or at about 95° C. for approximately 1 to 2 minutes with heat circulation; thickness of the chemistry matrix of 20 to 200 micrometers or less; at a pressure of 1 bar or 0.1 bar. Moreover, it will be understood that in order to keep the chemistry matrix under dry conditions, storage is, in an embodiment, carried out in the presence of a drying agent, i.e., a desiccant.

Suitable drying agents, in an embodiment, encompass silica gel, zeolites, calcium carbonate or magnesium sulfate.

As used herein, the term "active chemistry matrix" relates to a chemistry matrix of the present disclosure comprising the components as specified herein, including an enzymatic activity active in the presence of an analyte. Accordingly, the term "inactive chemistry matrix" relates to a chemistry matrix of the present disclosure not comprising said enzymatic activity active in the presence of said analyte. The inactive chemistry matrix of the present disclosure comprises at least the indicator reagent as referred to herein, in an embodiment, at the same concentration as it is present in the active chemistry matrix, and has a similar viscosity, in an embodiment, the same viscosity, as the active chemistry matrix. In a further embodiment, the inactive chemistry matrix comprises the same redox cofactor as the active chemistry matrix, in an embodiment, at the same concentration as it is present in the active chemistry matrix. Still in a further embodiment, the inactive chemistry matrix comprises the same film former as the active chemistry matrix, in an embodiment, at the same concentration as it is present in the active matrix. It is understood by the skilled person that for interference compensation to be as complete as possible, the active and the inactive chemistry matrix are typically as similar as possible, apart from the presence or absence of the enzymatic activity of the present disclosure. The inactive chemistry matrix of the present disclosure may have similar diffusion characteristics, or even the same diffusion characteristics, as the active chemistry matrix. Accordingly, in an embodiment, the composition of the active chemistry matrix differs from the composition of the inactive chemistry matrix only by the presence of said enzymatic activity in the active chemistry matrix. Also in an embodiment, the active chemistry matrix comprises a polypeptide having said enzymatic activity and the inactive chemistry matrix comprises a polypeptide not having said enzymatic activity. In a further embodiment, the polypeptide not having said enzymatic activity is an inactivated form of said polypeptide having said enzymatic activity. In a further embodiment, the polypeptide not having said enzymatic activity is a polypeptide being catalytically inactive, e.g., bovine serum albumin.

In an embodiment, the active chemistry matrix and the an inactive chemistry matrix are arranged in the sensor element such that an electrical circuit encompassing the first and second electrode and said active and inactive chemistry matrix can be closed after application of the test sample. In an embodiment, the active and inactive chemistry matrices are arranged adjacent to each other. In a further embodiment, the active and inactive chemistry matrices are arranged adjacent to each other such that both chemistry matrices are wetted by the test sample simultaneously. In a further embodiment, the active chemistry matrix and the inactive chemistry matrix are arranged in a face-to-face arrangement as described elsewhere herein.

As used herein, the term "enzymatic activity" relates to the activity of a biological molecule, in an embodiment, a biological macromolecule, in a further embodiment, a polypeptide, of catalyzing a chemical reaction. In an embodiment, the enzymatic activity is an oxidoreductase activity, in a further embodiment, a dehydrogenase activity. The term "dehydrogenase activity", as used herein, refers to an enzymatic activity catalyzing the oxidation or reduction of a substrate by transferring hydrides ($H^-$) in a one-step-mechanism or $H^+/e^-$ in a two-step mechanism as redox equivalents to or from a redox cofactor as referred to herein elsewhere. In an embodiment, a dehydrogenase activity catalyzes the oxidation of a substrate by transferring hydrides ($H^-$) as redox equivalents to an acceptor molecule, in an embodiment, to a redox cofactor as referred to herein elsewhere. Typical dehydrogenase activities are those which depend on a redox cofactor (or sometimes referred to as co-enzyme) such as pyrrolo quinoline quinone (PQQ), nicotinamide-adenine-dinucleotide (NAD) or a derivative thereof, or a flavine cofactor, such as flavin-adenine-dinucleotide (FAD) or flavine mononucleotide (FMN). Typical dehydrogenase activities are, in particular, those of the enzymes lactate dehydrogenase (EC number 1.1.1.27 or 1.1.1.28), glucose dehydrogenases (see below), alcohol dehydrogenase (EC number EC number 1.1.1.1 or 1.1.1.2), L-amino acid dehydrogenase (EC number 1.4.1.5), glycerin dehydrogenase (EC number 1.1.1.6), malate dehydrogenase (EC number 1.1.1.37), 3-hydroxybutyrate dehydrogenase (EC number 1.1.1.30), sorbitol dehydrogenase (EC number 1.1.1.14), or cholesterol dehydrogenase.

In a further embodiment, the dehydrogenase activity is the activity of a glucose dehydrogenase. In a further embodiment, said glucose dehydrogenase is selected from the group consisting of: glucose dehydrogenase (EC number 1.1.1.47), quinoprotein glucose dehydrogenase (EC number 1.1.5.2), in particular, pyrrolo quinoline quinone (PQQ)-dependent glucose dehydrogenase (EC number 1.1.5.2), glucose-6-phospate dehydrogenase (EC number 1.1.1.49), nicotinamide adenine dinucleotide (NAD)-dependent glucose dehydrogenase (EC number 1.1.1.119) and flavin adenine dinucleotide (FAD)-dependent glucose dehydrogenase (EC number 1.1.99.10) or enzymatically active mutants thereof.

Advantageously, it was found in the work underlying the present disclosure that by using a sensor element having a configuration of two electrodes, of which one contacts a chemistry matrix comprising an enzyme active in the presence of an analyte, and of which the second contacts a chemistry matrix not comprising said enzyme, and by measuring an electrical parameter once in a given polarity, followed by measuring in the inverted polarity, interference, i.e., signal not resulting from enzymatic activity on the analyte, can easily be compensated for. Reduction of the number of electrodes reduces overall measuring error and also reduces complexity of manufacture and, therefore, manufacturing costs.

The definitions made above apply mutatis mutandis to the following. Additional definitions and explanations made further below also apply for all embodiments described in this specification mutatis mutandis.

The present disclosure also relates to a method of detecting at least one analyte in a test sample, said method comprising the steps of a) contacting said test sample (i) to an active chemistry matrix changing at least one electrochemical property dependent on an enzymatic activity active in the presence of said analyte, said active chemistry matrix contacting a first electrode; and (ii) to an inactive chemistry matrix, said inactive chemistry matrix contacting a second electrode, b) closing an electrical circuit including said first and second electrode and said active and inactive chemistry matrix, followed by determining a first value of said at least one electrochemical property, c) inverting electrical polarity of the electrical circuit of b), followed by determining a second value of said at least one electrochemical property, and d) detecting said at least one analyte based on said first value and on said second value.

The method of the present disclosure, in an embodiment, is an in vitro method. Moreover, it may comprise steps in addition to those explicitly mentioned above. For example, further steps may relate, e.g., to obtaining a test sample for step a), or repeating steps b) and/or step c). Moreover, one or more of said steps may be performed by automated equipment.

The term "contacting" is understood by the skilled person and relates to bringing two elements into physical contact, allowing said elements or components thereof to interact.

The method of the present disclosure requires at least one measurement of a value of at least one electrochemical property in a given polarity, and at least one measurement of a value of said at least one electrochemical property in the inverse polarity. It is understood by the skilled person that said measurements may be repeated in order to increase accuracy of the result. Moreover, additional steps may be included, e.g., in an embodiment, one or more measurement and/or voltage free breaks between the measurements in the first and the second polarity. In an embodiment, said break is set to last for at least 0.5 s, in a further embodiment, for at least 1 s, still in a further embodiment, for at least 2 s, or, in a further embodiment, for at least 3 s. In an embodiment, the time range for said measurement and/or voltage free breaks is 0.1 s to 10 s, in a further embodiment, 1 s to 8 s or, in a further embodiment, 2 to 5 s. It is understood by the skilled person that, in case more than one measurement cycle is to be applied, measurement and/or voltage free breaks may be included also between said measurement cycles.

Advantageously, it was found in the work underlying the present disclosure, that an embodiment including a step of providing a voltage free break between the measurements in the first and the second polarity allows for reaction products, in particular redox products, in an embodiment, the redox indicator(s), to diffuse away from the electrodes. Thus, including said break reduces the current caused by the back-reaction of redox products formed at the electrodes, which might otherwise overlay the current induced by potentially present interfering compounds.

According to the present disclosure, any mathematical and/or metrological method suitable for compensating interference using said first and second value is usable for detecting an analyte of interest; e.g., a set of calibration curves may be established for specific pairs of first and second values; or the detection circuitry may be set up such that the signal generated by background chemical reactions is compensated for by the measuring device. Accordingly, it will not always be required that the value detected from background chemical reactions is actually put out to a user or to an evaluation unit. In an embodiment, detecting the analyte comprises calculating a difference between the first value and the second value determined according to the method of the present disclosure. Also in an embodiment, detecting the analyte comprises comparing the measured values to calibration data, said calibration data in an embodiment, having been obtained by determining training data under disturbed conditions, i.e., in an embodiment, in the presence of interfering compounds. In a further embodiment, detecting the analyte comprises calculating a weighted difference between the values measured applying the first and the second polarity, wherein the weighting factors are obtained by determining calibration data under disturbed conditions, i.e., in an embodiment, in the presence of interfering compounds.

In an embodiment, detecting an analyte with the method according to the present disclosure comprises applying a voltage, in a further embodiment, a DC voltage. In a further embodiment, detecting an analyte with the method according to the present disclosure comprises measuring the current resulting from said application of voltage. The voltage applied in the second polarity, in an embodiment, corresponds to the voltage applied in the first polarity ±40%, in a further embodiment, ±20%, or, still in a further embodiment, ±10%. In a further embodiment, the voltage applied has the same numerical value in both polarities.

It is understood by the skilled person that the method of the present disclosure can be put into practice using any device comprising the features specified. Accordingly, the method of the present disclosure may, e.g., in an embodiment, also be performed using a conventional test strip having more than two electrodes, of which at least one contacts a chemistry matrix comprising an enzymatic activity active in the present of an analyte, and of which at least one contacts a chemistry matrix not comprising an enzymatic activity active in the present of said analyte. In a further embodiment, the method of the present disclosure is put into practice using a sensor element of the present disclosure.

Moreover, the present disclosure relates to a test device for detecting at least one analyte in a test sample, comprising
 i) a receptacle for a sensor element, said sensor element comprising at least two electrodes and an active and an inactive chemistry matrix, said active chemistry matrix changing at least one electrochemical property dependent on an enzymatic activity active in the presence of said analyte, a first electrode contacting said active chemistry matrix; and a second electrode contacting said inactive chemistry matrix, and
 ii) means for determining the electrochemical property of at least one indicator reagent comprised in said sensor element according to the method of the present disclosure.

The term "test device", as used herein, relates to a test device in principle known in the art, however, adapted to measure the analyte-induced change of the electrochemical property as specified herein above according to the method of the present disclosure. Accordingly, the test device of the present disclosure comprises at least one receptacle for a sensor element and at least one means for determining an electrochemical property a chemistry matrix changing in the presence of an analyte, wherein said sensor element comprises (i) at least two electrodes and (ii) an active and an inactive chemistry matrix, said active chemistry matrix changing at least one electrochemical property dependent on an enzymatic activity active in the presence of said analyte; and wherein in said sensor element a first electrode contacts said active chemistry matrix; and a second electrode contacts said inactive chemistry matrix. In an embodiment, the test device of the present disclosure comprises at least one receptacle for a sensor element of the present disclosure.

In an embodiment, the test device further comprises a power supply unit, in an embodiment, a voltage source, e.g., in an embodiment, a battery and/or an accumulator, and/or an amperometer. In an embodiment, the test device is a diagnostic test device. In an embodiment, the test device further comprises at least one sensor for determining an ambient parameter. In a further embodiment, the test device further comprises at least one temperature sensor for determining an ambient temperature. Also in an embodiment, the test device is a hand-held test device.

The term "receptacle" is known to the skilled person and relates to an element of the test device shaped for receiving at least one sensor element, in an embodiment, a sensor element according to the present disclosure, providing one or more connectors and/or contacts as appropriate for detecting an analyte in a body fluid, and, in an embodiment, adapted to locate the test element in at least one application position in which a test sample of the body fluid is applicable to the test element. The specific embodiment of the test element receptacle will depend on the kind of test element and on the test chemistry used therein. Thus, as an example, the test element receptacle may be or may comprise one or more of: a slot for fully or partially inserting the at least one test element, in an embodiment, a strip-shaped test element; an open space within a housing to fully or partially receive the at least one test element; a magazine for receiving one or more test elements; a guiding for holding and/or moving one or more of the test elements.

It is understood by the skilled person that the test device of the present disclosure can be adapted to be used in conjunction with any sensor element comprising the features specified. Accordingly, the test device of the present disclosure may, e.g., also be adapted to be used in conjunction with a conventional test strip having more than two electrodes, of which at least a first electrode contacts an active chemistry matrix, and of which at least a second electrode contacts an inactive chemistry matrix. In a further embodiment, the test device of the present disclosure is adapted to be used in conjunction with a sensor element of the present disclosure.

Further, the present disclosure relates to a test system comprising
  i) a sensor element comprising at least two electrodes and an active and an inactive chemistry matrix, said active chemistry matrix changing at least one electrochemical property dependent on an enzymatic activity active in the presence of an analyte, a first electrode contacting said active chemistry matrix; and a second electrode contacting said inactive chemistry matrix, and
  ii) a device comprising a receptacle for the sensor element of a) and means for determining the electrochemical property of at least one indicator reagent comprised in said sensor element according to the method of the present disclosure.

Also, the present disclosure relates to the use of the sensor element according to the present disclosure, of the device according to the present disclosure, and/or of the system according to the present disclosure for detecting at least one analyte.

The disclosure further discloses and proposes a computer program including computer-executable instructions for performing the method according to the present disclosure in one or more of the embodiments enclosed herein when the program is executed on a computer or computer network. Specifically, the computer program may be stored on a computer-readable data carrier. Thus, specifically, one, more than one or even all of method steps a) to d) as indicated above may be performed by using a computer or a computer network, in an embodiment, by using a computer program.

The disclosure further discloses and proposes a computer program product having program code means, in order to perform the method according to the present disclosure in one or more of the embodiments enclosed herein when the program is executed on a computer or computer network. Specifically, the program code means may be stored on a computer-readable data carrier.

Further, the disclosure discloses and proposes a data carrier having a data structure stored thereon, which, after loading into a computer or computer network, such as into a working memory or main memory of the computer or computer network, may execute the method according to one or more of the embodiments disclosed herein.

The disclosure further proposes and discloses a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the disclosure proposes and discloses a modulated data signal which contains instructions readable by a computer system or computer network, for performing the method according to one or more of the embodiments disclosed herein.

In an embodiment, referring to the computer-implemented aspects of the disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the test samples and/or certain aspects of performing the actual measurements.

Specifically, the present disclosure further discloses:

A computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer program, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

All references cited in this specification are herewith incorporated by reference with respect to their entire disclosure content and the disclosure content specifically mentioned in this specification.

Summarizing the findings of the present disclosure, the following embodiments are envisaged:

Embodiment 1: A sensor element for determining at least one analyte, comprising a pair of electrodes and at least an active and an inactive chemistry matrix, said active chemistry matrix changing at least one electrochemical property dependent on an enzymatic activity active in the presence of said analyte, (i) wherein said pair of electrodes consists of two electrodes electrically insulated from other electrodes, (ii) wherein said active chemistry matrix comprises said enzymatic activity and wherein said inactive chemistry matrix does not comprise said enzymatic activity, and (iii) wherein a first electrode of said pair of electrodes contacts said active chemistry matrix and wherein a second electrode of said pair of electrodes contacts said inactive chemistry matrix.

Embodiment 2: The sensor element of embodiment 1, wherein the composition of said active chemistry matrix differs from the composition of said inactive chemistry matrix only by the presence of said enzymatic activity.

Embodiment 3: The sensor element of embodiment 1 or 2, wherein said active chemistry matrix comprises a polypeptide having said enzymatic activity and wherein said inactive chemistry matrix comprises a polypeptide not having said enzymatic activity.

Embodiment 4: The sensor element of embodiment 3, wherein said polypeptide not having said enzymatic activity is an inactivated form of said polypeptide having said enzymatic activity.

Embodiment 5: The sensor element of any one of embodiments 1 to 4, comprising exactly one pair of electrodes.

Embodiment 6: The sensor element of any one of embodiments 1 to 5, wherein said at least one analyte is glucose.

Embodiment 7: The sensor element of any one of embodiments 1 to 6, wherein said polypeptide having said enzymatic activity is a glucose dehydrogenase.

Embodiment 8: The sensor element of any one of embodiments 1 to 7, wherein said chemistry matrix further comprises at least one redox cofactor.

Embodiment 9: The sensor element of any one of embodiments 1 to 8, wherein the sensor element is a face-to-face sensor element.

Embodiment 10: A method of detecting at least one analyte in a test sample, said method comprising the steps of a) contacting said test sample (i) to an active chemistry matrix changing at least one electrochemical property dependent on an enzymatic activity active in the presence of said analyte, said active chemistry matrix contacting a first electrode; and (ii) to an inactive chemistry matrix, said inactive chemistry matrix contacting a second electrode, b) closing an electrical circuit including said first and second electrode and said active and inactive chemistry matrix, followed by determining a first value of said at least one electrochemical property, c) inverting electrical polarity of the electrical circuit of b), followed by determining a second value of said at least one electrochemical property, and d) detecting said at least one analyte based on said first value and on said second value.

Embodiment 11: The method of embodiment 10, wherein detecting said at least one analyte comprises calculating a difference between said first value determined in step b) and said second value determined in step c).

Embodiment 12: The method of embodiment 10 or 11, wherein step b) comprises applying a voltage to said electrical circuit.

Embodiment 13: The method of embodiment 12, wherein step c) comprises applying a voltage inverted relative to the voltage of step b) to said electrical circuit.

Embodiment 14: The method of any one of embodiments 10 to 13, wherein the voltage level applied in step b) is essentially the same as in step c).

Embodiment 15: A test device for detecting at least one analyte in a test sample, comprising (i) a receptacle for a sensor element, said sensor element comprising at least two electrodes and an active and an inactive chemistry matrix, said active chemistry matrix changing at least one electrochemical property dependent on an enzymatic activity active in the presence of said analyte, a first electrode contacting said active chemistry matrix; and a second electrode contacting said inactive chemistry matrix, and (ii) means for determining the electrochemical property of said at least one indicator reagent comprised in said sensor element according to the method according to any one of embodiments 10 to 14.

Embodiment 16: A test system comprising (i) a sensor element comprising at least two electrodes and an active and an inactive chemistry matrix, said active chemistry matrix changing at least one electrochemical property dependent on an enzymatic activity active in the presence of said analyte, a first electrode contacting said active chemistry matrix; and a second electrode contacting said inactive chemistry matrix, and (ii) a test device comprising a receptacle for the sensor element of a) and means for determining the electrochemical property of said chemistry matrices comprised in said sensor element according to the method according to any one of embodiments 10 to 14.

Embodiment 17: The system of embodiment 16, wherein the sensor element is a sensor element according to any one of embodiments 1 to 9.

Embodiment 18: Use of the sensor element according to any one of embodiments 1 to 9, of the test device according to embodiment 15, or of the test system according to embodiment 16 or 17 for detecting at least one analyte.

Embodiment 19: The sensor element of any one of embodiments 1 to 9, wherein said sensor element does not comprise a reference electrode.

Embodiment 20: The sensor element of any one of embodiments 1 to 9 and 19, wherein said pair of electrodes is insulated from any additional electrode potentially present in said sensor element such that (i) the resistance between the first electrode of the pair of electrodes and any additional electrode and (ii) the resistance between the second electrode of the pair of electrodes and any additional electrode, both are at least 25 Id2 after application of a test sample to the sensor element.

Embodiment 21: The method of any one of embodiments 10 to 14, put into practice using a sensor element according to any one of embodiments 1 to 9 and 19 to 20.

In order that the embodiments of the disclosure may be more readily understood, reference is made to the following examples, which are intended to illustrate but not limit the scope thereof.

In FIG. 1, a schematic view of an exemplary embodiment of a sensor element 110 is depicted. In this exemplary embodiment, the sensor element 110 is designed as a test strip. However, additionally or alternatively, other types of sensor elements 110 may be used, such as test tapes and/or test discs.

Figure 2:
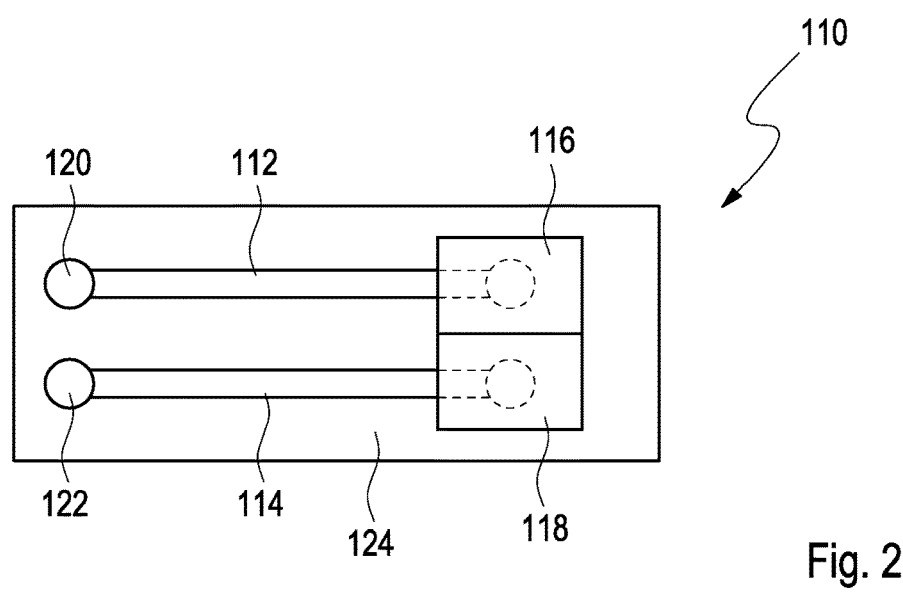
FIG. 2 shows a schematic top view of another exemplary embodiment of a sensor element according to the present disclosure.

The sensor element 110, as outlined above, comprises at least one first electrode 112 contacting an active chemistry matrix 116; and at least one second electrode 114 contacting an inactive chemistry matrix 118. The first electrode 112 and the second electrode 114 are both located on a substrate 124 as a support layer. It is understood by the skilled person that the sensor element 110 may also be embodied in a closed form, wherein the sensor element comprises a capillary element guiding the test sample 126 to the active chemistry matrix 116 and to the inactive chemistry matrix 118. The active chemistry matrix 116 and the inactive chemistry matrix 118 can be in direct contact to each other (as shown in FIGS. 1A-B and 2) or, in alternative embodiments of the disclosure, spaced apart from each other. The first electrode 112 comprises at an end which is not covered by the active chemistry matrix 116 a contact element of the first electrode 120. The second electrode 114 comprises at an end which is not covered by the inactive chemistry matrix 118 a contact element of the second electrode 122. These contact elements 120, 122 can be used to conductingly connect the sensor element 110 to a measuring unit for determining the analyte.

The exemplary sensor element 110 depicted in FIG. 2 comprises the same elements as the exemplary sensor element depicted in FIGS. 1A-B. However, the spatial arrangement of the elements is different.

Figure 3:
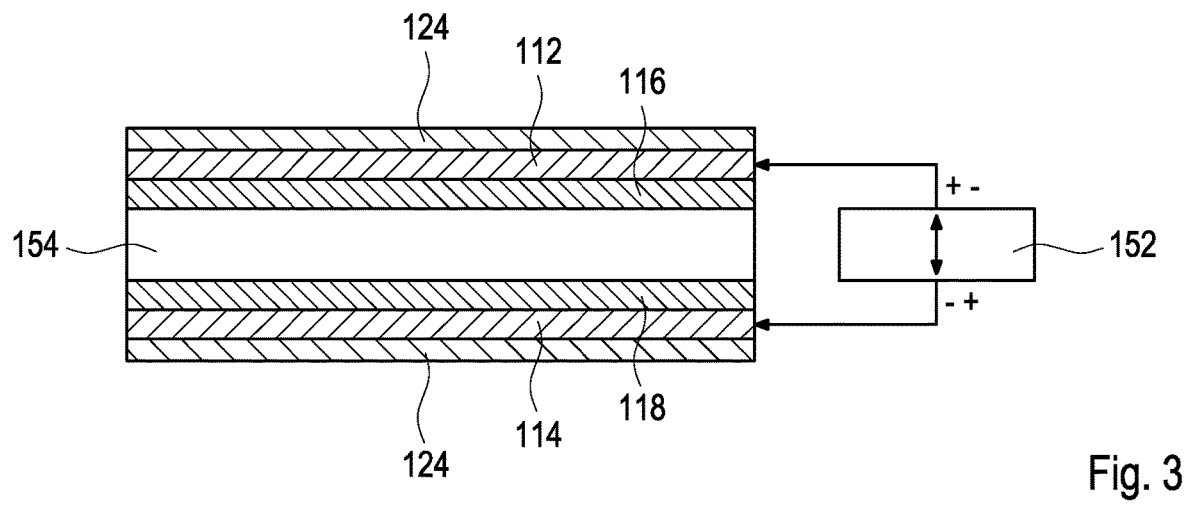
FIG. 3 shows a schematic cross-sectional view of a face-to-face electrode setup connected to a potentiostat.

In FIG. 3, a schematic cross-sectional view of another exemplary embodiment of a sensor element 110 is depicted. In this exemplary embodiment, the sensor element 110 is designed in a face-to-face configuration. The face-to-face sensor element 110 comprises the same elements as the sensor element of FIG. 1 or 2, however, the first electrode 112 contacting the active chemistry matrix 116 and the second electrode 114 contacting the inactive chemistry matrix 118 are arranged in an opposing orientation. The first electrode 112 and the second electrode 114 are both located on substrates 124 as their respective support layers. The sample can be located within the sample chamber 154 between the first electrode 112 and the second electrode 114 and is in contact to both electrodes 112, 114. The sample chamber can comprise capillary dimensions which allow the sample to flow into and fill the sample chamber by capillary actions. A potentiostat 152 is used to apply voltages of defined polarity and magnitude to the first electrode 112 and second electrode 114.

Figure 4:
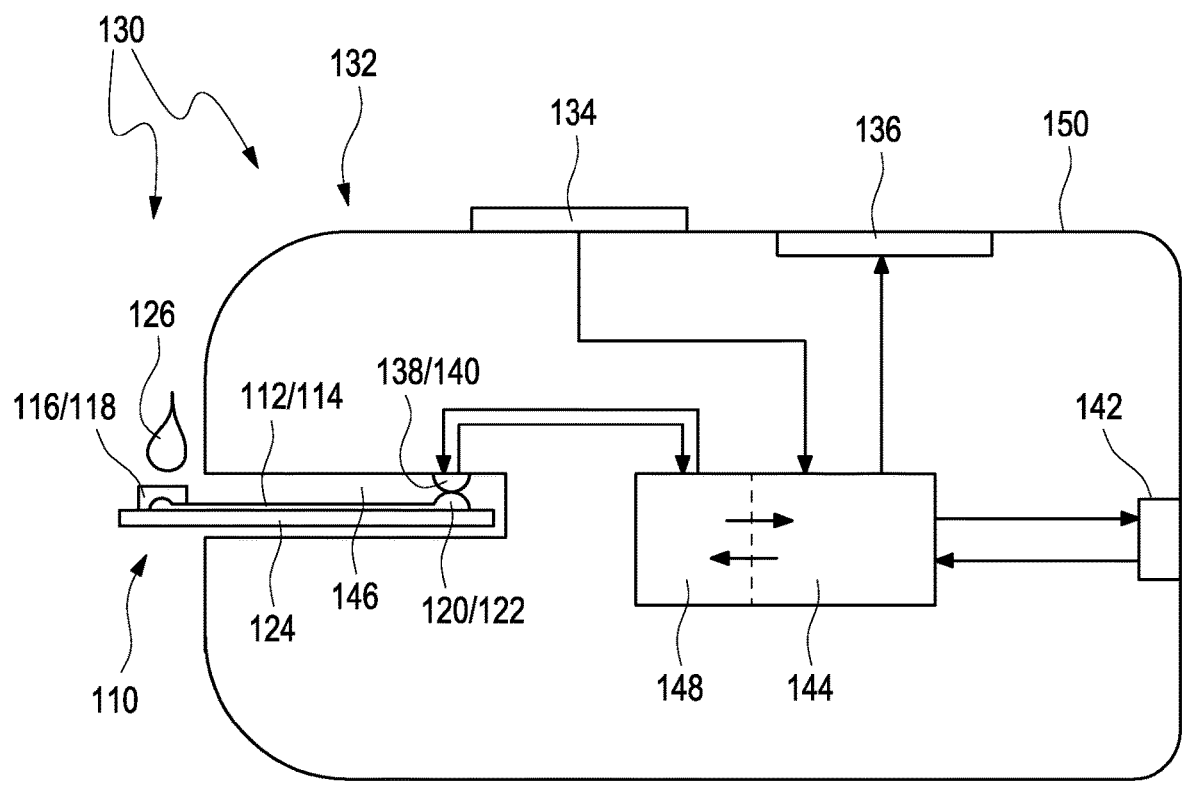
FIG. 4 shows a schematic cross-sectional view of an exemplary embodiment of a test system and a test device of the present disclosure.

In FIG. 4, a cross-sectional view of an embodiment of a test device 132 and a test system 130 according to the present disclosure is depicted. The test device 132, in an embodiment, is embodied as a hand-held device. The test device 132, in an embodiment, comprises a casing 150, which may have a volume of less than 1000 cm$^3$, in an embodiment, of less than 500 cm$^3$, in order to be carried by a person. The test device 132 comprises a receptacle 146 for receiving a sensor element 110, which, besides the test device 132, forms a component of the test system 130. The receptacle 146 is adapted to locate the sensor element 110 in at least one application position in which a test sample 126 of a body fluid is applicable to the sensor element 110.

The test device 132 further comprises a measuring unit 148 measuring the change in an electrochemical property of the active chemistry matrix 116 and the inactive chemistry matrix 118 comprised in the sensor element 110. To this end, the measuring unit is conductingly connected to the first electrode 112 via the contact element of the first electrode 120 and the contact element contacting the contact element of the first electrode 138, and to the second electrode 114 via the contact element of the second electrode 122 and the contact element contacting the contact element of the second electrode 140.

The test device 132 further comprises at least one evaluation unit 144 which is adapted to determine the concentration of the analyte by using the values measured by the measuring unit 148. The evaluation unit 144, in an embodiment, may be or may comprise at least one data processing device, such as at least one computer and/or at least one application-specific integrated circuit.

As an example, the evaluation unit 144 may comprise a microcomputer. Further, the evaluation unit 144 may comprise one or more further elements, such as at least one data storage device and/or other components.

The evaluation unit 144 is unidirectionally or bidirectionally connected to the measuring unit 148, such as for receiving measurement values from the measuring unit 148. Further, the evaluation unit 144 may be adapted to control the overall functionality of the test device 132, such as for controlling the measurement process performed by the measuring unit 148.

The test device 132 may further comprise one or more human-machine-interfaces, such as at least one display 136 and/or at least one control element 134, such as at least one push button. The elements 134, 136 may also be connected to the evaluation unit 144.

The test device 132 may further comprise at least one electronic interface 142, for unidirectional and/or bidirectional exchange of data and/or commands with one or more external devices, such as a wireless and/or a wire-based interface.

Figure 5:
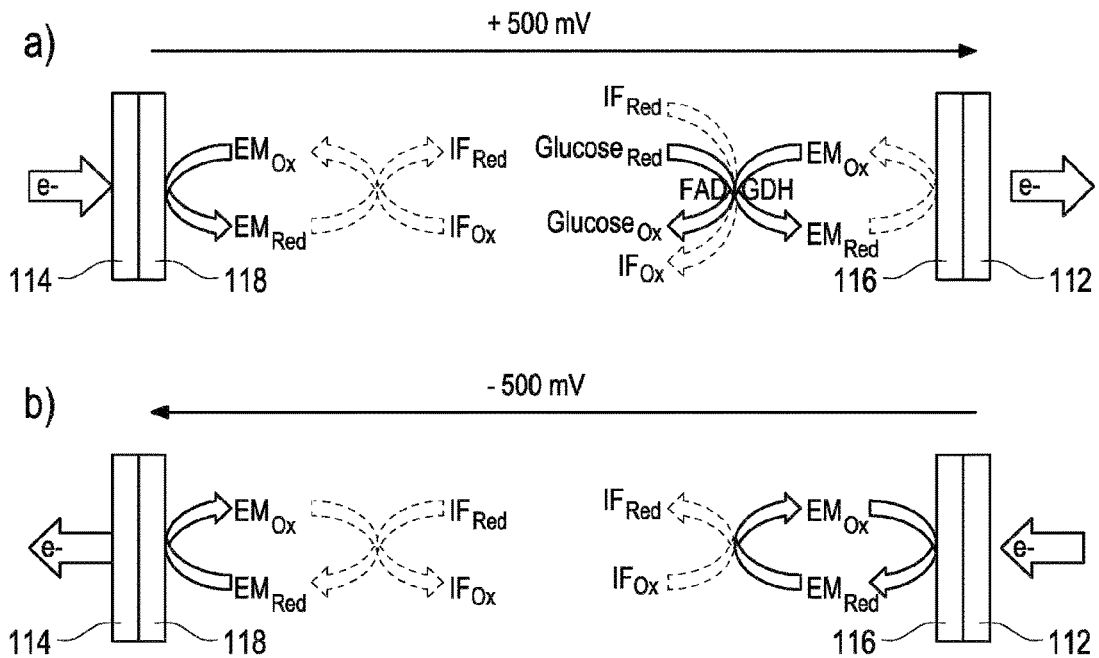
FIG. 5 shows a schematic representation of the underlying principle of the interference compensating measurement of the present disclosure—EM: indicator reagent (electromediator), IF: interfering compound (redox-active); the contribution of the interfering compound is the same in both polarities, whereas glucose only contributes to the current measured if a positive voltage is applied.

FIG. 5 shows a schematic representation of the underlying principle of the interference compensating measurement of the present disclosure. First electrode 112 contacts the active chemistry matrix 116, and second electrode 114 contacts the inactive chemistry matrix 118. In the active chemistry matrix 116, glucose is oxidized by the enzyme glucose dehydrogenase (GDH) to produce reduced flavine-adeninedinucleotide (FAD); in the inactive chemistry matrix 118, in the absence of GDH, glucose is not oxidized and no reduced FAD is produced. Thus, in the polarity of FIG. 5a), glucose and an interfering compound (IF) contribute reduction of the indicator reagent (electro-mediator, EM) and, thus, to the current measured. In contrast, in the polarity of FIG. 5b), only the IF can contribute to the current. Thus, the contribution of the interfering compound is the same in both polarities (+500 mV and −500 mV)), whereas glucose only contributes to the current measured if a positive voltage is applied.

Figure 6:
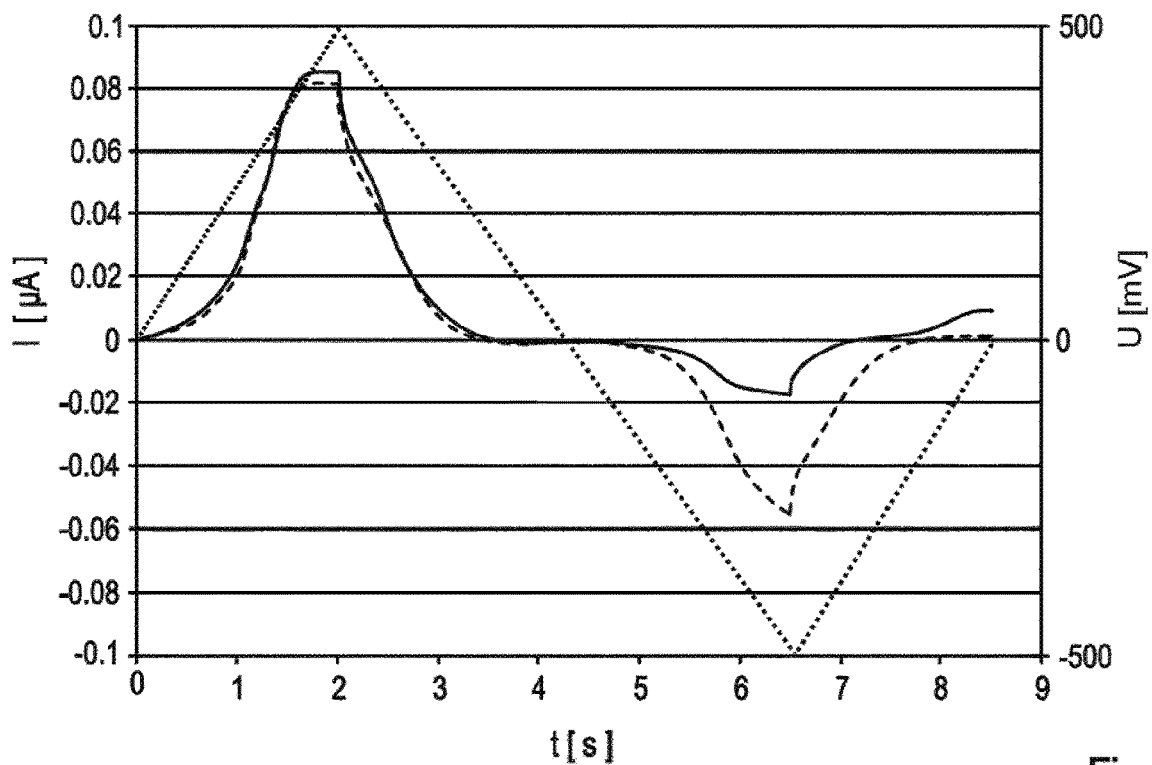
FIG. 6 shows a graph representing the current measured after applying the voltage indicated between the two electrodes on a test element according to the present disclosure—x-axis: time (t) in s, y-axis: current (A) measured in µA or Voltage (U) applied in mV. Dotted line: voltage applied; solid line: current measured using a solution with 120 mg/dL glucose as a sample, dashed line: current measured using a solution with 30 mg/dL glucose+30 mg/dL ascobic acid as a sample.
Figure 7:
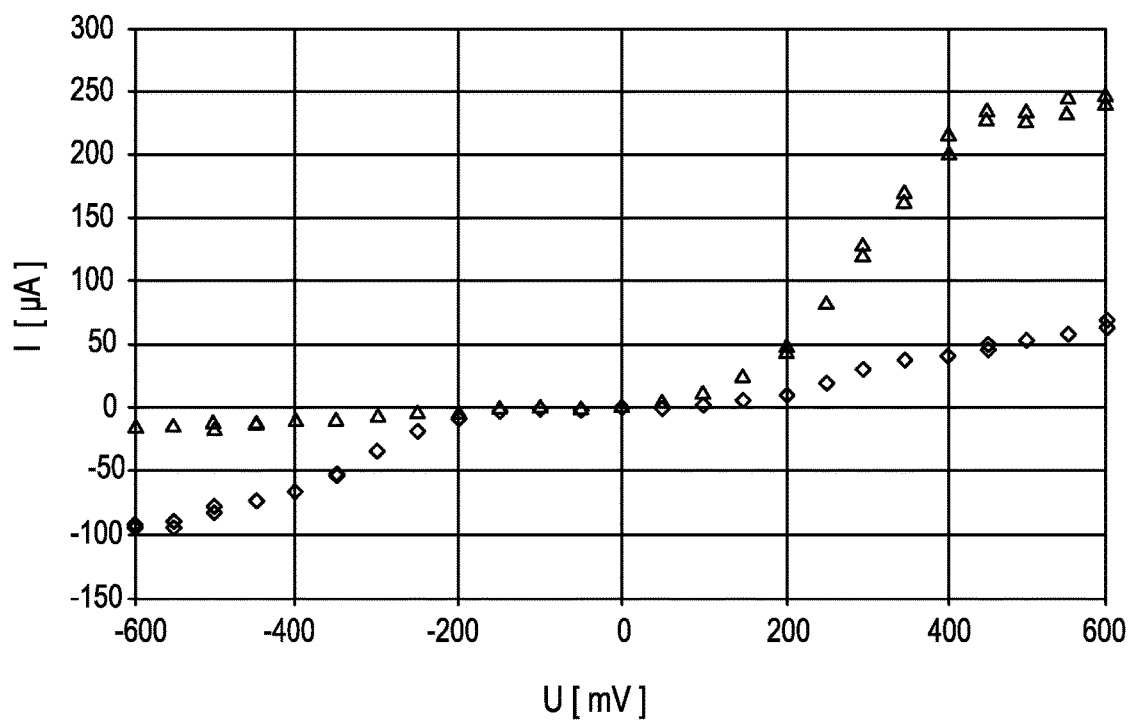
FIG. 7 shows a graph representing the current measured after applying the voltage indicated between the two electrodes on a test element according to the present disclosure—x-axis: voltage (U) applied in mV, y-axis: current (I) measured in µA, sampling time t=5 s; samples were: triangles: glucose (600 mg/dL); diamonds: ascorbic acid (100 mg/dL). Two test strips were measured for each sample.
Figure 8:
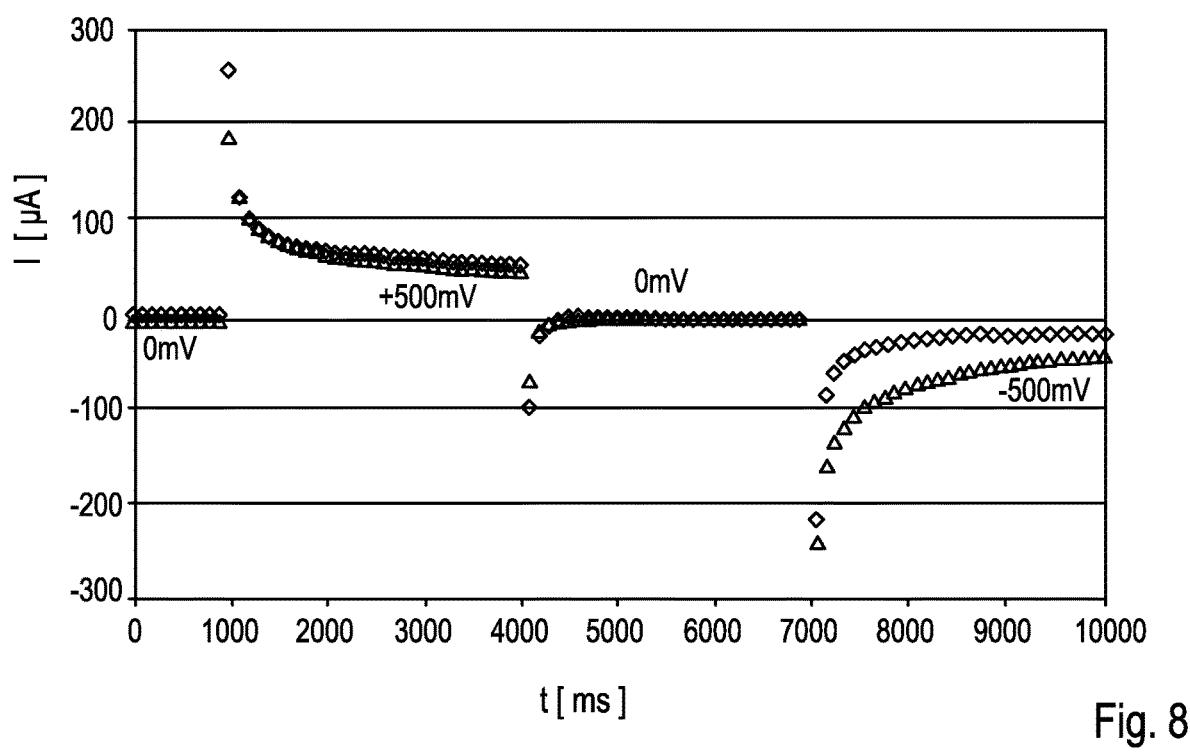
FIG. 8 shows a graph representing the current measured after applying and holding the voltage indicated between the two electrodes on a test element according to the present disclosure—x-axis: time (t) applied in ms, y-axis: current (I) measured in µA; diamonds: current measured using a solution with 120 mg/dL glucose as a sample, triangles: current measured using a solution with 30 mg/dL glucose+30 mg/dL ascobic acid as a sample.

The graphs in FIGS. 6-8 show the results of a dynamic measurement on face to face test strips implementing the interfering compensation of the present disclosure. The test setup used disposable face to face electrode test strips corresponding, in principle, to the setup depicted schematically in FIG. 3: Using polyester foil as a substrate (support) 124, 50 nm sputtered gold was deposited as first and second electrode 112, 114 and approximately 5 gm of chemistry matrix 116, 118 was applied (thickness measured after drying). Chemistry matrices comprised conventional thickeners, film formers, buffer compounds, detergents, and stabilizers and the like known in the art; the redox mediator used was a nitrosoaniline. The enzyme used in the active chemistry matrix 116 was a glucose dehydrogenase (GDH) using FAD as a cofactor; in the inactive chemistry matrix 118, GDH was replaced by albumin. The dimensions of the sample chamber were 0.2 mm×2 mm×10 mm; accordingly, the distance between the first electrode 112 and the second electrode 114 was 0.2 mm.

Example 1

In the example of FIG. 6, a triangular voltage signal is applied to the electrodes. Compared are test results with a glucose solution and a solution containing glucose and the interfering compound ascorbic acid. When the enzyme electrode, i.e., the electrode contacting the active chemistry matrix, is positively polarized, the response from glucose and the interfering substance cannot be differentiated. In the reverse polarity, on the other hand, it can be clearly separated. By analyzing the current response from both polarities in combination with a suitable calibration including the test substance (e.g., glucose) and the interfering substance (e.g., ascorbic acid), a signal largely independent from the interfering substance can be calculated.

Example 2

The FIG. 7 shows the result of a static current-voltage experiment on face to face interfering compensation electrodes. Here, for different voltages in the range from −600 to +600 mV every 50 mV an amperometric measurement on an each time new disposable test strip were performed. The used indicator reagent was a nitrosoaniline redox indicator and the enzyme was a glucose dehydrogenase. When a glucose containing sample gets in contact with the enzyme containing reagent, the nitrosoaniline gets reduced to a phenylene-diamine, which than can be oxidized on the positive polarized electrode. On the second electrode, which does not contain the enzyme, the nitrosoaniline is reduced directly on the negative polarized electrode. So for this direction of the electrodes polarization both electrode supports an electron transfer and a resulting current can be measured. When the polarization is reverse, only the negatively charged electron can support an electron transfer by reducing the nitrosoaniline. At the now positive polarized enzyme free electrode no phenylenediamine is present and therefore no electron transfer is supported. As a result no current can be measured.

If instead of the glucose containing sample the experiment is repeated with ascorbic acid, a current response is received for both directions of the polarization. Nitrosoaniline gets reduced by the ascorbic acid independently of whether the glucose-dehydrogenase enzyme is present or not.

The same interfering compensation method can be used, if an interfering substance directly interacts with the electrode and not indirectly with the redox-mediator. If for both polarization directions the current response from the interfering substance electrode reaction is measured, this than can be used to correct the actual analytical test (e.g., a glucose concentration measurement) in combination with a suitable algorithm and calibration.

Example 3

FIG. 8 shows an example of a test sequence implementing the reverse polarity test phases.

In a first part of the test sequence (1000 ms-4000 ms in FIG. 8) the polarity is polarizing the enzyme containing electrode positively. The applied voltage is +500 mV. If a glucose containing sample is dosed to the test strip, an amperometric current response can be measured. On the positive electrode the phenylene-diamine produced by the enzyme reaction delivers electrons to the electrode. On the negatively polarized electrode the nitrosoaniline gets reduced and takes the electrons from the electrode. In a second measurement phase (4000 ms-7000 ms in FIG. 8) a zero voltage is applied to the electrodes. Without the polarization no electrode reaction occurs for the used electrode system. Accordingly, the redox reaction products have time to re-diffuse from the electrode reaction zone, so that when the electrodes are polarized to the reverse polarity, the resulting current response from the reaction products generated in the first step is minimized. As a third amperometric step (7000 ms-10000 ms in FIG. 8), the reversed polarity is applied (500 mV related to the working electrode here defined by enzyme containing electrode). In the example, a glucose containing solution (120 mg/dL) is compared to the result received with a glucose and ascorbic acid containing sample (30 mg/dL and 30 mg/dL). It can be seen, that at the positive polarization (1000 ms-4000 ms in FIG. 8) the two samples cannot be clearly differentiated, whereas with the inverse polarity (7000 ms-10000 ms in FIG. 8) a clear difference can be found.

LIST OF REFERENCE NUMBERS 110 sensor element
112 first electrode
114 second electrode
116 active chemistry matrix
118 inactive chemistry matrix
120 contact element of first electrode
122 contact element of second electrode
124 substrate (support)
126 test sample
130 test system
132 test device
134 control element
136 display
138 contact element contacting contact element of first electrode
140 contact element contacting contact element of second electrode
142 interface
144 evaluation unit
146 receptacle
148 measuring unit
150 casing
152 potentiostat
154 sample chamber

What is claimed is:

1. A sensor element for determining at least one analyte, comprising a pair of electrodes and at least an active chemistry matrix and an inactive chemistry matrix, said active chemistry matrix changing at least one electrochemical property dependent on an enzymatic activity active in the presence of said analyte,
   (i) wherein said pair of electrodes consists of two electrodes which remain electrically insulated from other electrodes after application of a test sample,
   (ii) wherein said active chemistry matrix comprises said enzymatic activity and wherein said inactive chemistry matrix does not comprise said enzymatic activity, each of the active chemistry matrix and the inactive chemistry matrix comprising an indicator reagent capable of eliciting a change in at least one electrochemical property in the presence of redox equivalents, and
   (iii) wherein a first electrode of said pair of electrodes contacts said active chemistry matrix and wherein a second electrode of said pair of electrodes contacts said inactive chemistry matrix.

2. The sensor element of claim 1, wherein the composition of said active chemistry matrix differs from the composition of said inactive chemistry matrix only by the presence of said enzymatic activity.

3. The sensor element of claim 1, wherein said active chemistry matrix comprises a polypeptide having said enzymatic activity and wherein said inactive chemistry matrix comprises a polypeptide not having said enzymatic activity.

4. The sensor element of claim 1, wherein said analyte is glucose.

5. The sensor element of claim 1, wherein said analyte is comprised in a test sample.

6. The sensor element of claim 5, wherein said analyte is comprised in a blood test sample.

7. The sensor element of claim 1, wherein each of said pair of electrodes is insulated from any additional electrode present in said sensor element such that (i) the resistance between the first electrode and any additional electrode and (ii) the resistance between the second electrode and any additional electrode, are at least 25 kΩ after application of a test sample to the sensor element.

8. The sensor element of claim 1, consisting of exactly one pair of electrodes.

9. The sensor element of claim 1 wherein said sensor element does not comprise a reference electrode.

10. The sensor element of claim 1 wherein said active and inactive chemistry matrices are arranged such that both chemistry matrices are wetted by the test sample simultaneously.

11. The sensor element of claim 1, wherein the first and second electrodes are arranged in a face-to-face configuration.

12. The sensor element of claim 1, wherein the first and second electrodes are configured to receive thereon a test sample contacting both the active chemistry matrix and the inactive chemistry matrix.

13. The sensor element of claim 12, wherein further including a capillary element guiding a fluid test sample to the first and second electrodes.

14. The sensor element of claim 13, wherein the first and second electrodes are received within the capillary element and are arranged in a face-to-face configuration.

15. A test device system for detecting at least one analyte in a test sample, comprising:
(i) a receptacle for receiving a sensor element;
(ii) a sensor element received within the receptacle and comprising a first electrode and a second electrode, at least an active chemistry matrix, and at least an inactive chemistry matrix, the active chemistry matrix changing at least one electrochemical property dependent on an enzymatic activity active in said chemistry in the presence of said analyte, the first electrode contacting said active chemistry matrix comprising said enzymatic activity, and the second electrode contacting said inactive chemistry matrix not comprising said enzymatic activity; and
(iii) a measuring unit in electrical contact with the first and second electrodes of the sensor element when received within the receptacle, the measuring unit applying a first voltage across the electrodes followed by a second voltage of opposite polarity across the electrodes, and measuring the changes in the at least one electrochemical property during the application of each of the first and second voltages and generating first and second outputs related thereto.

16. The test device system of claim 15 and further comprising a data processing device operable to receive the first and second outputs from the measuring unit and to detect said at least one analyte based on the first and second outputs.

17. A test device system for detecting at least one analyte in a test sample, comprising:
a receptacle for receiving a sensor element;
a sensor element received within the receptacle and comprising a first electrode, a second electrode, an active chemistry matrix, and an inactive chemistry matrix, each of the active chemistry matrix and the inactive chemistry matrix comprising an indicator reagent capable of eliciting a change in at least one electrochemical property in the presence of redox equivalents, the active chemistry matrix changing at least one electrochemical property dependent on an enzymatic activity active in said chemistry in the presence of said analyte, the first electrode contacting said active chemistry matrix and the second electrode contacting said inactive chemistry matrix,
the sensor element comprising a capillary element, the first and second electrodes being received in the capillary element in a face-to-face configuration, the electrodes being configured to provide electrical communication therebetween upon introduction of the test sample into the capillary element,
the first and second electrodes being insulated from any additional electrode sensors in the sensor element after application of a test sample;
a measuring unit in electrical contact with the first and second electrodes of the sensor element received within the receptacle and forming an electrical circuit with the first and second electrodes upon contact of the test sample with the active chemistry matrix and the inactive chemistry matrix; and
a data processing device operable to receive the output from the measuring unit and to determine the at least one analyte based on the output.

18. The test device system of claim 17, wherein the composition of said active chemistry matrix differs from the composition of said inactive chemistry matrix only by the presence of said enzymatic activity.

19. The test device system of claim 17, wherein said active chemistry matrix comprises a polypeptide having said enzymatic activity and wherein said inactive chemistry matrix comprises a polypeptide not having said enzymatic activity.

20. The test device system of claim 17, wherein said analyte is glucose.

21. The test device system of claim 17, consisting of exactly one pair of electrodes.

22. The test device system of claim 21, wherein further including a capillary element guiding a fluid test sample to the first and second electrodes.

23. The test device system of claim 17, wherein the first and second electrodes are received within the capillary element and are arranged in a face-to-face configuration.

* * * * *